Figure 1:
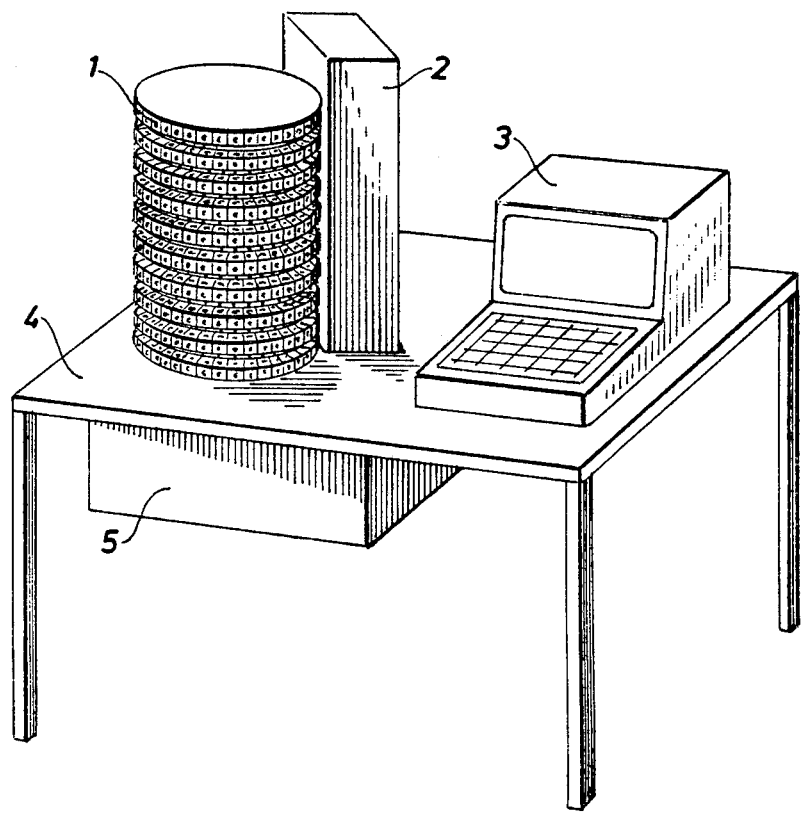

United States Patent [19]

Rolfo-Fontana

[11] 3,932,131

[45] Jan. 13, 1976

[54] METHOD AND DEVICE (ANALYSIS MACHINE) FOR SIMULTANEOUS PERFORMANCE OF A NUMBER OF ANALYSES, ESPECIALLY MICROANALYSES, OF STANDARD TYPE ON CHEMICAL OBJECTS

[75] Inventor: Gudrun Birgitta Margareta Rolfo-Fontana, Monte-Carlo, Monaco

[73] Assignee: Monega Anstalt, Vaduz, Liechtenstein

[22] Filed: June 27, 1974

[21] Appl. No.: 483,621

[30] Foreign Application Priority Data
Feb. 7, 1974 Sweden ........................... 7401657

[52] U.S. Cl. .............. 23/230 R; 23/253 R; 141/25; 141/92; 141/130
[51] Int. Cl.² .................... B67C 3/00; G01N 31/00; G01N 31/18
[58] Field of Search .......... 23/230 R, 230 B, 253 R, 23/259; 195/103.5, 127; 141/25, 92, 130

[56] References Cited
UNITED STATES PATENTS

| | | | |
|---|---|---|---|
| 3,484,206 | 12/1969 | Loebl | 23/259 X |
| 3,544,272 | 12/1970 | Vaills | 23/253 R |
| 3,575,692 | 4/1971 | Gilford | 23/253 R |
| 3,617,222 | 11/1971 | Matte | 23/230 R |

Primary Examiner—Robert M. Reese

[57] ABSTRACT

Methods and apparatus for the simultaneous performance of a series of analyses upon a multiplicity of samples disposed in an upright array of cuvette receptacles therefor, said array being in mating facial juxtaposition with similarly disposed arrays of reagent dispensing means, sample dispensing means, treatment means, analytic means and receptacle cleaning means such that individual operative means are coordinately positioned for simultaneous engagement with a plurality of receptacles; and executing steps in the analytic sequence by moving the receptacle array to a series of spaced positions sequentially whereby individual receptacles are simultaneously progressed in a series of steps through a cycle of sample treatment and analysis to cleaning.

14 Claims, 10 Drawing Figures

METHOD AND DEVICE (ANALYSIS MACHINE) FOR SIMULTANEOUS PERFORMANCE OF A NUMBER OF ANALYSES, ESPECIALLY MICROANALYSES, OF STANDARD TYPE ON CHEMICAL OBJECTS

The invention relates to a method for simultaneous performance of a number of analyses, especially microanalyses, of standard type on chemical (clinical, biological, agricultural or industrial chemical) objects (patient samples, food samples, water samples, soil samples) as also for a device (analysis machine) for performance of the method.

The invention relates especially to simplification of the entire analysis procedure in the laboratory by using, for qualitative and quantitative microanalysis of very small quantities of substance, unit reagent doses especially prefabricated and exactly measured for the purpose.

Chemical analysis, i.e. the establishment of the nature and quantity of the constituents of a specific sample substance by use of chemical or physico-chemical methods, especially microanalysis, has extremely great practical importance, especially within medicine and within public health and environmental protection, for food control within agricultural and within the chemical industry.

In such an analysis one makes use of every observable property of the element the occurrence of which in a given substance is to be established. It is primarily a question of the mode of reaction of the element, i.e. whether one can produce with it, for example, a colour which can be measured or whether the concentration of the element can be established through its catalytic (e.g. enzymatic) effect. But in addition the colour, for example, of the element itself can be determined, or its solubility, density, electrical conductivity, emission and absorption of light, the effect on it of polarized light, its refraction index, crystal structure, atomic configuration, etc. The number of possible methods of analysis in each particular case is thus dependent on the number of such properties of the element.

The kinds of analysis which may be of interest are dependent, apart from the sample material, also on the intention of the analysis.

Of most interest in conjunction with the invention are so-called wet chemical analysis methods, i.e. methods in which chemical reactions are performed in solutions. Sample and reagent are in this case treated by means of volume measurements, i.e. with pipettes, burettes and other measuring vessels. The event in the solution can then be followed by different methods, such as photometric, spectrophotometric, fluorimetric, turbidimetric, nephelometric, polarimetric or other optical methods. These are the commonest methods for clinical analysis.

There is, however, a great need for exact volumes of reagent also for electrochemical analysis methods, e.g. methods in which one uses specific ion electrodes or measures electrical conductivity, or methods such as polarography and electrometrical titrations.

Also for the serological methods, especially important for medicine, in which for example, one wishes to find the agglutinizing capacity of blood corpuscles or precipitation of antigen-antibody aggregates, one can use reagent unit doses. Certain bacteriological analyses are also dependent on an exactly dispensed reagent.

For all the aforementioned kinds of analysis the usual procedure at present is to use reagents in the form of solutions, the reagent solution being added by pipetting.

But strict demands must be placed on the accuracy of measurement of the quantity of reagent solution added to the investigated substance. Especially as a result of the increasing automation of laboratory work in recent years it is desirable to limit the number of samplings on patients and to subject the samples taken to increasing numbers of analyses. This has the result that the quantity of substance available for each analysis becomes increasingly smaller. Consequently the quantity also of reagent solution added to each sample must also be measured in increasingly small volumes under simultaneous observation of satisfactory accuracy. Using the current pipetting procedures one can at present, by automatic technique, measure liquid volumes down to about 30 $\mu$l within an error of below $\pm$ 1 percent.

It appears impossible to come below these figures with conventional devices, owing to the capillary effect, drops at the tip of the pipette, small leakages etc.

According to the present invention an attempt to solve the difficulties is made though decentralization of the part of the analysis work relating to the measurement of the reagent by transferring this work to specialized pharmacological enterprises, so that in the laboratory one has access to small, accurately measured unit reagent doses.

The reason for this is that it has been found that smaller doses of, inter alia, reagents can be achieved with simultaneous increase of the accuracy by changing the physical properties of the solution, such as its viscosity, through the effect of temperature or vacuum, blasting and/or addition or inert substances, so that the reagents are obtained in gelatinized or more or less dry form and that the dispensing thereafter takes place by mechanical division or sectioning. Additions of agar-agar mixtures, pectins, gelatine and various cellulose derivatives have given good results.

One can also scrape off drops of the liquid with higher viscosity, expressed from the tip of a pipette with the aid of a corrugated band or the like which is thereafter cut into pieces along the corrugations.

One may also imagine that on a band fed past the tip of a pipette, drops of the reagent solution with elevated viscosity are applied, the which are thereafter left to dry, after which the strip is divided into pieces with one or more drops in each piece.

Another method is, by means of a pipette, to apply a continuous bead of a liquid with elevated viscosity, of constant width and thickness, on a band fed past the tip of the pipette and thereafter, by microsectioning, to cut the band and the bead of reagent applied to it in accurately proportioned units.

Finally one may conceive of filling a very thin-walled tube of plastic or the like with a gelatinized reagent liquid, after which the thin tube with the solidified reagent liquid is sectioned into thin, accurately proportioned discs. If so desired, the influence exerted on the physical properties of the liquid can, alternatively or simultaneously, be effected by means of blasting or cooling.

By changing the physicochemical properties of solutions in this way the handling of the reagent is transferred from handling by means of pipettes to handling by means of apparatus for treatment of highly viscous or gelatinous bodies in the same way as is done, for example, in microsectioning for preparation of tissue specimens for microscopic investigation. Surprisingly, one thereby attains an accuracy of dossage which exceeds that in the dispensing of low-viscosity liquids by several orders of magnitude. At the same time the advantage is gained that every dispensed dose can be added to the corresponding sample substance separately, in contra-distinction to the case of pipetting, in which the pipette must be used for a series of different samples, whereby some risk of pollution arises, a risk which is avoided through the present invention.

Through the virtual elimination of pipetting in the analysis work it is possible to use a unit cuvette both as sample vessel and measuring vessel, which implies that, in contradistinction to known procedures, in which the same cuvette has been used for different samples, the invention allows the use of different cuvettes for different samples, which is made possible through the fact that a microcomputer is used to make individual corrections for optical dissimilarities in the cuvettes. Through this use of a unit cuvette an extremely simple analysis procedure and an extremely compact and simple analysis machine is obtained.

The method according to the invention is thus essentially characterized in that a number of reagent vessels (cuvettes) are first arranged along an essentially vertical coordinate surface, the cuvettes for the different kinds of analysis forming essentially horizontal planes (one or more) and the individual cuvettes on the various planes assuming positions one above the other, so that for each object (patient sample etc.) an essentially vertical column of cuvettes is formed, that the various columns are thereafter moved stepwise laterally in relation to a likewise essentially vertical feed unit (tower) marking the starting position of the coordinate surface, that for each step a basic solution is first dispensed into the cuvettes in the first column, that thereafter, possibly in the next step of said column, unit doses of reagent intended for a first object, accurately measured in advance and bound to carriers, are dispensed into the cuvettes in the first column, while at the same time basic solution is dispersed into the cuvettes in a second column, and that finally possibly in a third step, accurately measured microdoses of sample substance relating to the first object are dispensed into the cuvettes in the first column, while at the same time accurately measured unit doses of reagent relating to a second object and bound to carriers are dispensed into the cuvettes in the second column and basic solution is simultaneously dispensed into the cuvettes in the third column and so on, that the reaction in the various cuvettes is allowed to proceed during the stepping operation, that the carrier, suitably after a number of dispensing steps (possibly corresponding to the analysis with the longest reaction time), is removed from the cuvettes, that thereafter the desired optical (photometric, spectrophotometric, nephelometric, fluorimetric, turbidimetric, polarimetric) measurement is performed by radioscopy of the cuvettes in a measuring step, and that finally the reaction mixture in all cuvettes in a column is suctioned off and the cuvettes are cleaned with washing liquid in order to be reusable in new sample analyses.

The reaction mixture in the various cuvettes should preferably be agitated during the stepping procedure. Likewise the temperature of the reaction mixture in the various cuvettes should preferably be regulated during the stepping procedure so as to obtain the desired reaction process (incubation). The coordinate surface may suitably consist of a cylinder, so that each column of cuvettes completes one revolution when an analysis process has been completed.

According to the invention the dispensing of at least the basic solution and reagent unit, but appropriately also the sample substance, can take place in the same step.

Through the use of reagent units with carrier bodies the advantage is gained that the carrier body constitutes a sort of intermediate body between the dispensing device and the cuvette, so avoiding contamination.

The carrier bodies should preferably contain magnetic material so that, after they have been introduced into the cuvettes, through the application to the cuvettes of a pulsating or alternating magnetic field, the bodies can be caused to move up and down in their cuvettes and thus agitate the reaction mixture.

According to the invention the reaction temperature in the cuvettes can also be regulated by means of heating or cooling elements (Peltier effect). For this purpose one may possibly use the impulse currents which generate the alternating magnetic field.

The time for stepping of the columns of cuvettes is so chosen that the reaction process in all cuvettes on the various planes has been completed when the cuvette cylinder has completed one revolution.

In an appropriate position of the column, optical measurement can be done through the reaction mixture and the cuvettes after the carrier has been removed from the cuvette by magnetic means.

According to a modification of the invention the sample substance can also be dispensed in the manner described above for the reagent or can be fed out by a syringe pipette in exact quantities into a row of carriers containing magnetic material and movable in a path past the mouth of the syringe pipette, after which the carriers are brought up one by one to an elevator in the feed unit or the tower and, by means of magnetically operating lift arms on the elevator, are taken up to the various cuvette planes in the column of cuvettes allotted to the object until all cuvettes of the column have been filled with sample substance, after which the columns of cuvettes are fed forward one step and the process is repeated for a new object.

The aforesaid carriers may appropriately be included in prefabricated reagent units absorbing exact doses of reagent, the sample substance fed out in exact quantities being absorbed by an inert absorbent placed on the carriers or within recesses which may be arranged on their covers.

The invention also relates to a device (analysis machine) for performance of the method, characterized chiefly in that the reagent vessels (the cuvettes) for the analyses are arranged along an essentially vertical coordinate surface, the cuvettes for the various types of analyses forming essentially horizontal planes (one or more) and the individual cuvettes on the various planes being placed one above the other, so that for each object (patient sample etc.) they form an essentially vertical column of cuvettes, in addition to which the various columns are arranged to be moved stepwise laterally in relation to a likewise essentially vertical feed unit (tower) marking the starting point of the coordinate surface, the which feed unit has elevating devices, which in engagement with feed-ways are arranged to deliver to the cuvettes in the various columns of objects accurately measured quantities of sample substance in preferably tubular carriers containing magnetic material, and possibly sealed with a cover, as well as stacks of feed devices which, by means of cassettes inserted at different planes corresponding to the planes of the cuvettes, successively during stepping of the columns feed the cuvettes on the various planes with reagent units intended for the respective type of analysis.

In operation the sample substance for a given object is, through for example, a syringe pipette driven by a synchronous motor and furnished with a plunger, fed out in exact quantities into a row of tubular carriers movable in a path past the mouth of the syringe pipette and containing magnetic material. The individual carries may by means of their upper edge, scrape off drops of sample substance fed to the mouth of the pipette. These carriers are brought up one by one to an elevator in the feed unit and are carried up by the elevator by means of magnetically operating arms to the various cuvette planes in the column of cuvettes allotted to the object until all cuvettes in the column have been filled with sample substance, after which the columns of cuvettes are stepped forward one step and the process is repeated for a new object.

The coordinate surface may in such case well form a cylinder, each column of cuvettes, after termination of an analysis process, completing one revolution of the cylinder.

The cylinder may be either of metal, such as aluminum, or of plastic and furnished with planes consisting of a number of rings of, for example, aluminum arranged one above the other at a given mutual spacing, appropriately formed of several segments, the rings being provided at fixed mutual distances round their periphery with seatings for the cuvettes, and the plastic cylinder, at least at its lower edge, being provided with a driving gear-ring which during its rotational movement, slides in an axial bearing on the base of the cylinder, possibly through the action of spokes and hubs on the gear-ring. If desired, the rings can have a meander-shaped contour and, on the various planes, can be mutually displaced one step so that access to a cuvette on a lower plane can take place through a meander gap in the plane above.

To permit optical measurement through the cuvettes the cuvette seatings have through-holes running radially in relation to the cylinder surface. By means of a microcomputer the result can then be corrected according to optical peculiarities of the cuvettes. The cylinder wall can also advantageously have through-holes arranged immediately above the cuvette seatings to allow access to the cuvettes by means of pipettes from the inside of the cylinder.

The device can also appropriately be furnished with a device for adjusting the energy content of the impulses in order thereby to regulate the reaction temperature in the cuvettes.

For service of the cuvettes the device according to the invention may be characterized also in that the feed unit or tower is arranged along the outer side of the coordinate surface in close association with it and that the elevating means of the tower and the stack of feed means are provided with individual access means corresponding to the various cuvette levels, the access means at each step of the coordinate surface (cylinder surface) supplying the cuvettes in a given column of objects with reagent units or measured doses of sample substance, the movement of all access means of the tower to active feed position in towards the cuvettes being simultaneous and parallel, so that several columns of cuvettes are served simultaneously.

Meanwhile the movement of the access means is achieved by movement of the entire tower in towards the cylinder surface under movement in parallel with itself.

The feed unit also has access means for optical measurement on cuvettes, e.g. when they have completed their cycle of analyses, and access means also for supply of basic solution to or washing and flushing of the cuvettes.

According to one embodiment of the invention the analysis machine is also characterized in that, to permit service of the cylinder also from its inside the cylinder has, within its periphery, an internal feed unit or internal tower on its base provided both with pipettes for supply of basic solution to the cuvettes and with nozzles for washing and flushing of the cuvettes, and finally with access means provided with sources of light for optical measurement against light-sensitive elements on corresponding access means on the outer tower.

On the external and internal towers all feed, measurement and flushing means required for starting and termination of the analysis processes may appropriately be concentrated, all means after a completed revolution of a cylinder being actuated simultaneously by means of the common drive units of the two towers.

The main principles for the invention are thus the following:

1. Extreme simplicity of the entire mechanical system

The number of moving parts, including pipettes, photometers etc., has been considerably reduced compared with earlier known systems.

2. Extreme decentralization of components and functions

Everything which is not absolutely necessary to have in the vicinity of the analysis machine or all procedures which can be carried out prior to the analysis and/or elsewhere have been removed from the analysis procedure of conventional type.

3. Supervision of the stability of the machine

To attain a higher degree of precision and repeatability, exact supervision and control are maintained of the temperature in the reagent vessels and of the other functions of the machine.

4. Through the use of microcomputers (analogue, hybrid or digital) the reaction tube equipment has been reduced to a minimum Computer operations can often be performed at an early stage. A simplified printout may suffice if the analysis machine is connected to a larger computer.

5. Extreme simplification of the movements of the analysis machine

The concentration of similar components into large units which are moved jointly and simultaneously, and the use of very simple and reliable functional methods, increase the reliability. Ease of access for supervision of the various parts of the machine has also been taken into account.

The invention will now be described with reference to the attached drawings, which show the following:

FIG. 1 the chief parts of an analysis machine according to the invention

Figure 2:
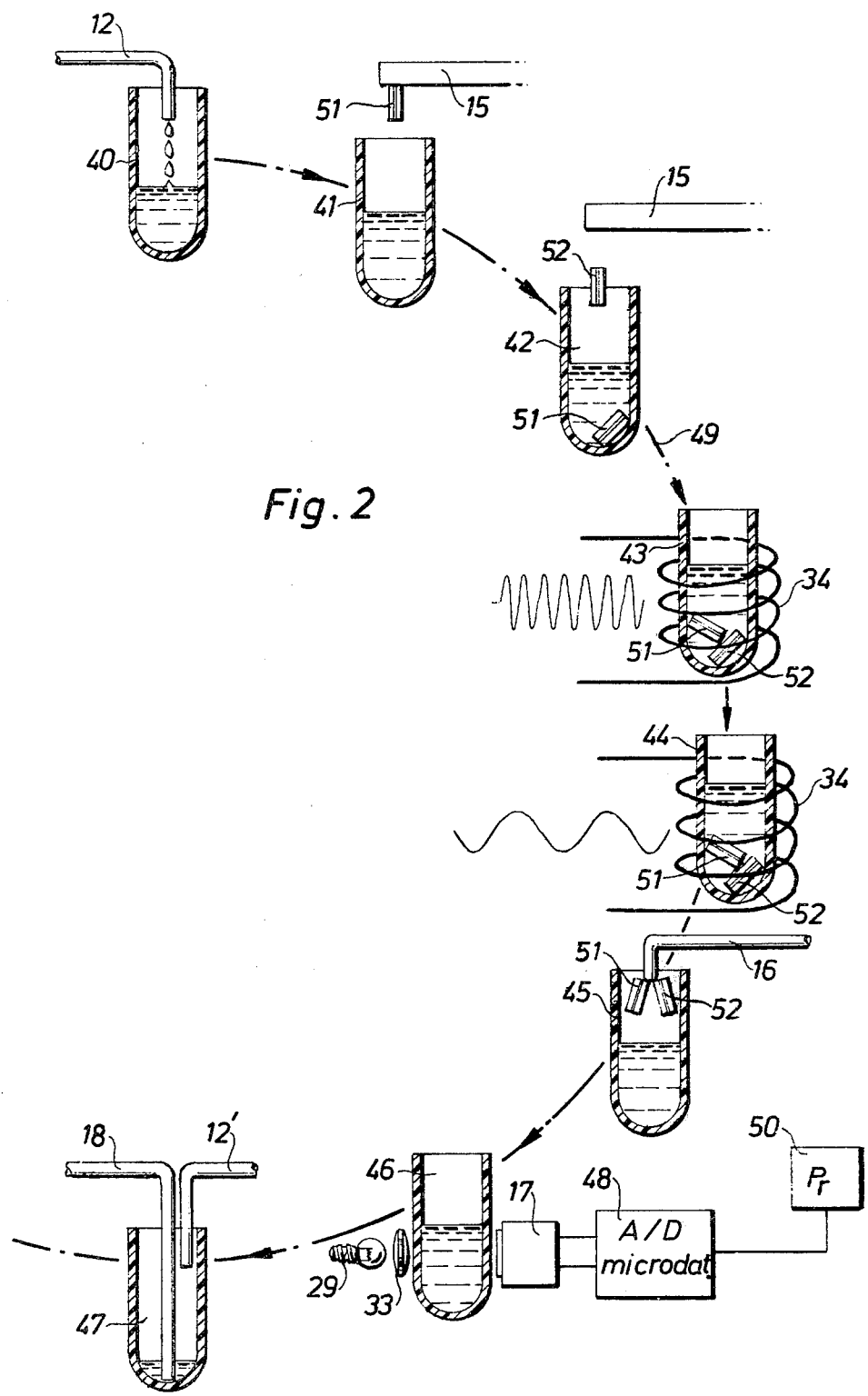
Figure 3:
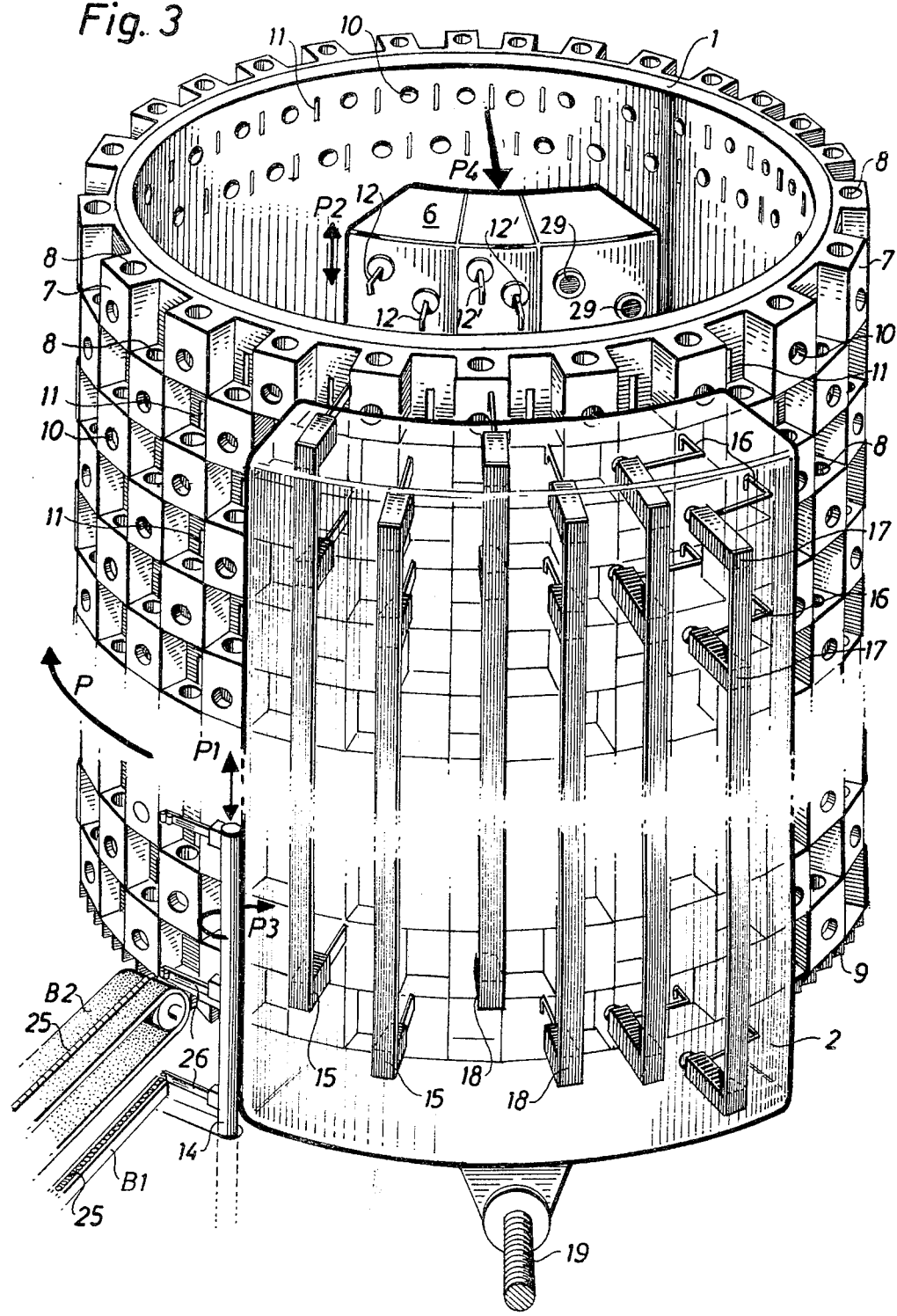
Figure 4:
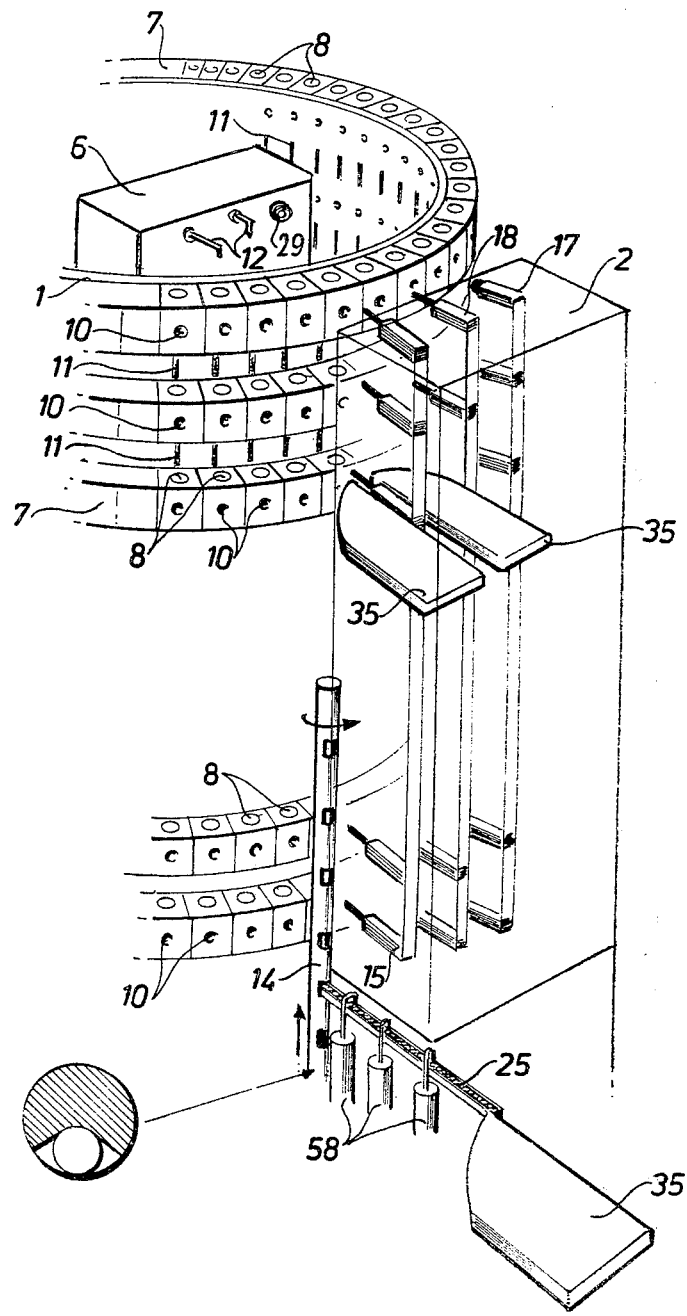
Figure 5:
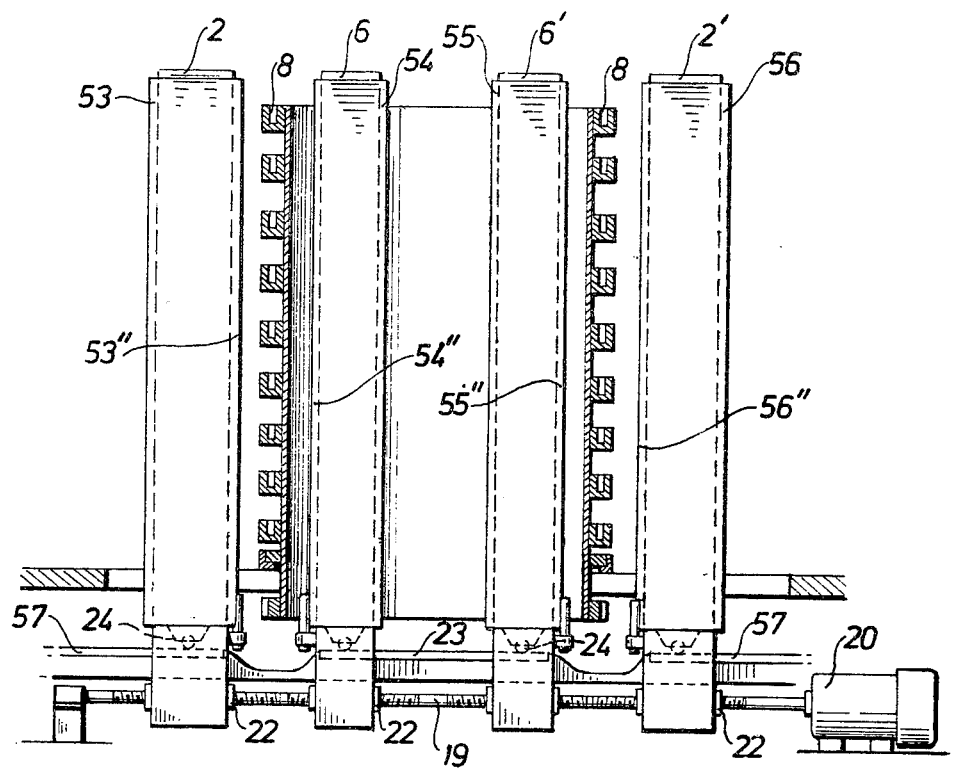
Figure 6:
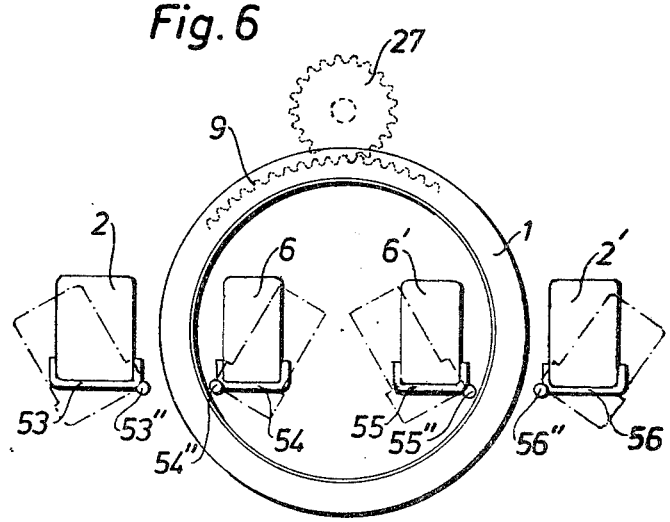
Figure 7:
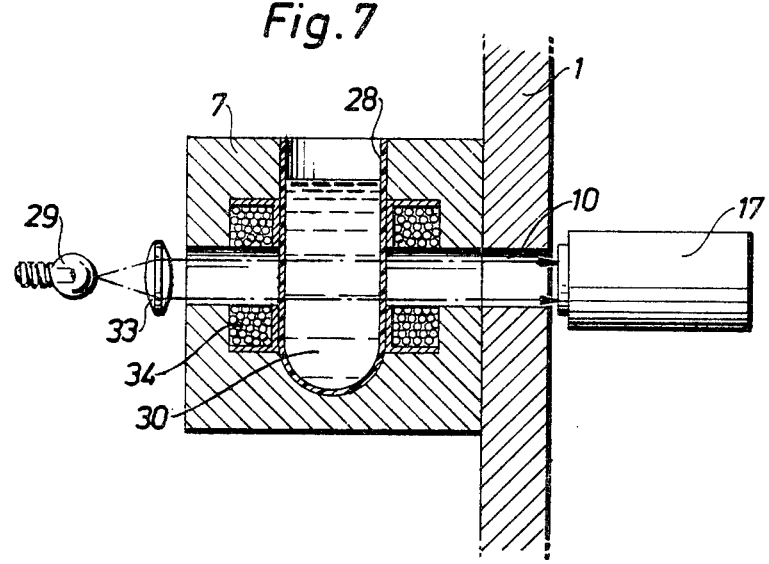
Figure 8:
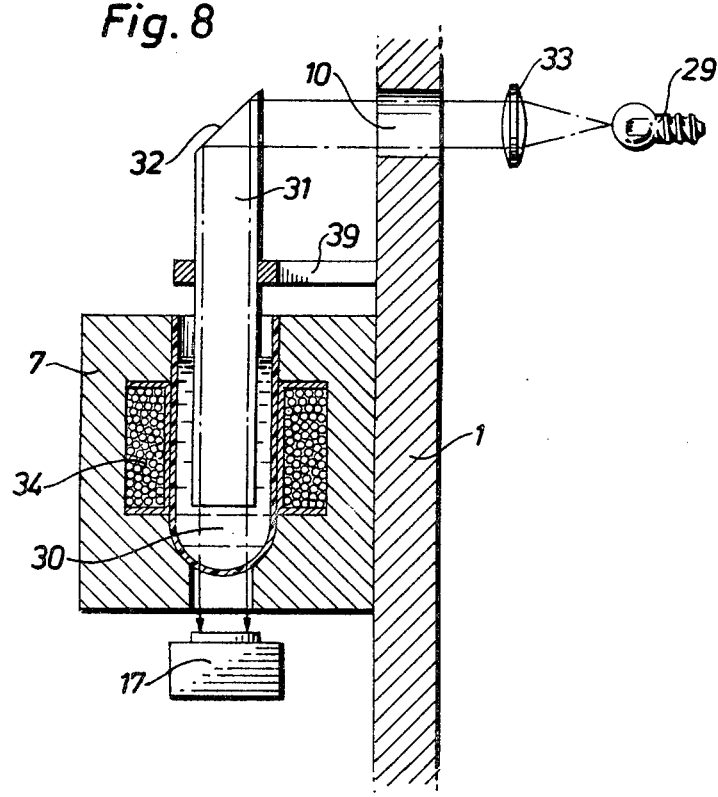
Figure 9:
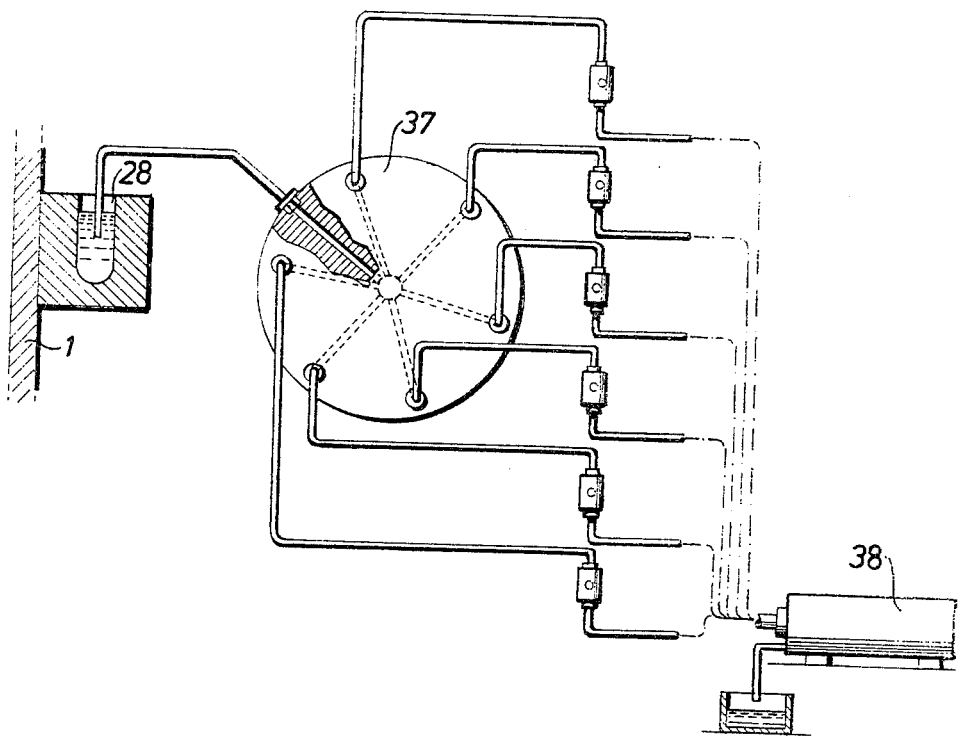
Figure 10:
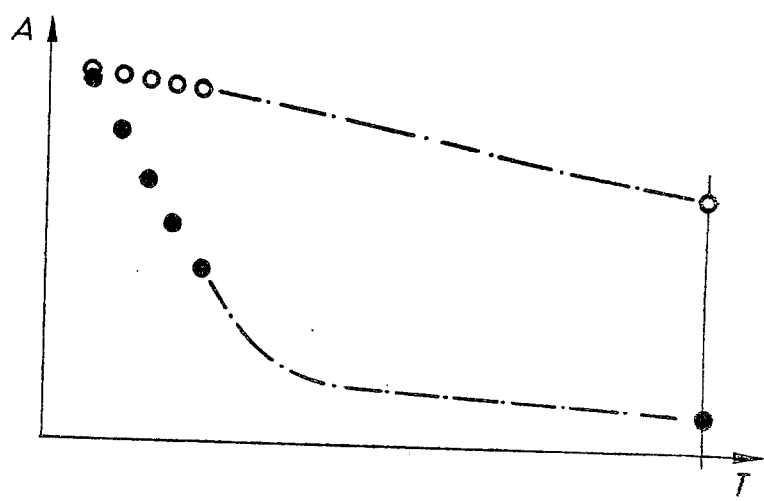

FIG. 2 a schematic picture of the operations which occur in the procedure according to the invention and with the analysis machine according to the invention FIG. 3 in perspective an analysis cylinder according to one embodiment of the invention FIG. 4 another embodiment of the same FIGS. 5 and 6 schematically how the analysis cylinder and its external and internal feed units or towers can be moved FIGS. 7 and 8 two different ways for direct photometry in the reagent cuvettes, while FIG. 9 shows how so-called kinetic photometry can take place in conjunction with an analysis process, and FIG. 10 a diagram in which the various measurement points from a so-called kinetic photometry measurement have been introduced.

As appears from FIG. 1, the analysis machine according to the invention consists essentially of the following parts.

A cylinder 1, which on its outer surface carries a large number of sample cuvettes.

A feed unit or tower 2, on the outside or inside of cylinder 1, or on both sides, which can dispense the components necessary for the analysis.

A stand or table 4 to carry the cylinder 1, tower 2, and their motor 5.

A plastic casing, not shown in the drawing, which covers the cylinder and towers, and a supervisory unit 3 with multiplexor and device for write-out of the results.

In conjunction herewith some general points of view concerning the analysis machine according to the invention may be adduced.

The analysis machine is intended to deal only with samples which have been pretreated in a specific way. Also most chemicals which are used in the analysis machine are intended to be predispensed by means of equipment not belonging to the analysis machine.

The outside of the cylinder carries horizontal rings, each of which is divided into four segments. Each ring is used as a holder for sample cuvettes in a row round the cylinder, each ring being assigned for one kind of chemical analysis. The rings for the various kinds of analysis are arranged one above the other on different planes, so that the height of the cylinder limits the number of possible analyses, which usually is 25–50.

The analysis machine is intended to perform solely the following movements:

Stepping of the cylinder in one direction from one position to the next.

Movement of the towers so that the components can be brought up to the cuvettes on the various planes of the cylinder. The tower on the inside of the cylinder is also moved as an independent whole, so that its components simultaneously reach the desired position, i.e the intended sample cuvette.

In this way a very simple analysis machine is obtained with few parts, which, however, since they are concentrated into a relatively small volume, must be capable of release for inspection, which is done by lifting of the plastic casing and raising the entire cylinder with its cuvettes from the base, after which the towers can be swung out by means of a simple movement so that their sets of components, which are arranged in vertical rows, can be inspected and examined.

The following principles of construction have therefore been adopted in the invention.

A. As noted, a large number of moving parts have been combined so that the movement of a large number of similar parts takes place at one time. This implies, for example, that turning of a body, which contains a large number of components, by means of a simple and reliable movement simplifies the machine as a whole, although it has been necessary to move a large number of components.

In the application of this principle to the cylinder, which comprises a number of rings arranged one above the other, intended as holders for the sample cuvettes, the advantage is gained that all cuvettes in the cylinder assume new positions on movement of the cylinder one step.

Another important application of this principle is that a large number of moving parts, which distribute the sample substance and reagent, as also the washing and rinsing devices together with the measuring equipment, are combined into feed units — the inner and outer tower — which are moved in their entirety.

B. To reduce the number of pipettes required, reagents are used in the form of unit doses intended for use in conjunction with a given sample. This means that one uses prefabricated reagent units which are dispensed with high precision. In this way the work in the analysis machine is reduced to handling extremely small quantities of reagent and to ensuring agitation of the reaction mixture, whereas the responsibility for high reproducibility and extreme exactness in respect of the reagent doses has been transferred to their manufacturer.

C. Since the analysis procedure is directed to very small volumes (1 up to 200 $\mu$l) it is possible to reduce the distance of transport for the solutions which are to be dispensed or measured. This necessitates special devices for measurement, which implies among other things that the sample cuvettes in the cuvette rings of the cylinder can be reached both from a feed unit on the inside of the cylinder through the cylinder wall and from a feed unit on the outside.

D. The final measurement operation, generally photometry, can be done in different ways. In principle one can use individual lamps for each sample, but it is also conceivable to use large lamps with light distributed by means of fibre optics or halogen lamps, tungsten band lamps, hydrogen gas lamps, etc.

E. The extreme concentration of the functions in the analysis machine according to the invention makes it possible and desirable to use individual microcomputers for different tests, which at an early stage convert the results of the measurement into the desired form.

In FIG. 2 are shown schematically a number of important operations which it is intended shall be performed according to this method of analysis. The various operations are illustrated schematically in relation to a number of reaction tubes 40–47 movable along an imaginary path 49. The various tubes are imagined to be situated in specific working positions. Tube 40, for example, is in a position where basic solution is dispensed by means of a feed pipette 12. Tube 41 is imagined to be in a position where the measured quantity of sample is to be added. Before this can be done, the samples must first be collected, marked and arranged and thereafter measured, e.g. by means of a sample pipette, e.g. in the way indicated above in respect of the reagent doses.

The sample is thereafter transported, bound to a carrier 51 on a conveyer belt, not shown in FIG. 2, and in an elevator, and is fed down into cuvette 41 by means of an arm 15 on the elevator. In the next analysis position a tube 42 is situated in which there is already basic solution and a sample carrier 51. Into the latter a carrier 52 for reagent is fed down in a similar manner by means of an arm 15. In the next working position is a tube 43, where carriers 51 and 52 which contain magnetic material are shown. The carriers contain sample substance and reagent. The mixture is agitated since the tube is surrounded by a coil 34 which is supplied with pulsating current or impulses of alternating direction.

In another working position is shown a tube 44, the coil 34 of which is supplied with prolonged pulses which thereby at the same time heat the tube and its content.

From tube 45, which is imagined to be in a final position on path 49, carriers 51, 52, which are then empty, are raised by means of a magnetically acting device 16.

With reference to tube 46 shown in a subsequent position, it is shown how direct photometry can be done through the tube with a lamp 29, lens 33 and a photocell 17. The measured values from the photocell are taken to an A/D micro-computer 48 and thence to a printer 50.

Finally, at the end of path 49 is shown a tube 47, in which flushing liquid is introduced through a nozzle 12' and suctioned off through a hose 18.

The reaction thus proceeds during the main part of the movement of the tubes, incubation taking place at a constant temperature. Heat regulation is achieved, as already mentioned, by regulating the duration of the agitation impulses.

At the termination of the reaction, measurement is done either as indicated above by direct photometry through the tube, in which case the microcomputer corrects for any optical perculiarities in the tube, or by means of transmission to, for example, a multipath photometer for so-called kinetic photometry.

On completion of the measurement washing and flushing of the tube take place as shown.

The chief analysis operations in this analysis procedure are the following:
1. Sample measurement technique
2. Addition of reagent in different ways
3. Reaction tubes, cuvettes,
4. Incubation as regards time and temperature
5. Agitation
6. Photometry (if a colour has developed) or other measuring procedure
7. Washing and drying.

The common principle for transfer of a given quantity of sample for analysis or for dispensing of reagent is that the additions to the reaction tubes are prepared, i.e. measured and bound to carriers, so that they can be easily and reliably handled by the machine.

Since sample substance and reagent must generally be added in highly viscous form, an initial quantity of liquid — basic solution — is needed, which may be pure water or a simple salt or buffer solution to which sample and reagent are to be added.

The intended chemical reaction proceeds in a reaction tube, called a cuvette if the vessel furthermore has optically ground walls to allow light measurements on light rays passing through the solution.

The carrier or carrier body generally consists of short plastic tubes with magnetic material in their walls. It must either be able to receive a small quantity of sample and transport it to the reaction tube or be able to contain a reagent dose which will likewise be taken to the reaction tube. Alternatively the carrier body must be able to receive both the reagent dose and a small quantity of sample and carry them both to the cuvette. Finally it must be able to perform the mixing in the cuvette, which is an important element in the present method of analysis and which is achieved through the fact that the magnetic field from an electric coil surrounding the cuvette alternates through intermittent activation from electrical impulses. The carriers may be formed in such a manner as to be enclosed with covers which then of course must be opened as by a gripper device. The devices may, for example, open the carrier covers and lower the carriers into the cuvette.

7. Sample Measurement

The procedure which at present is considered to be most exact, and is therefore most used for addition of a small but exactly measured volume of the sample material intended for analysis, is carried out with a so-called dilutor. For this purpose the desired volume is suctioned up into a narrow tube, appropriately of hydrophobic plastic, and the sample is later extruded with a specific quantity of diluent liquid which at the same time flushes the tube clean for new use. This procedure presumes that a considerable dilution is always effected, which sometimes is very advantageous, and that the time is extended, since the dispensing of sample must await the addition of diluent.

According to the invention it is not necessary to add any diluent in the dispensing of the sample, and one therefore avoids this delay.

For the actual measurement of the sample there are three courses, depending on the size of the sample. For the largest volumes, more than 30 $\mu$l, an injection syringe is used which is filled with, for example, blood serum and is so manoeuvred that predetermined quantities are dispensed for each analysis. For a smaller volume the sample is suctioned up into a thin-walled plastic tube which is cut into lengths corresponding to the desired volumes for different analyses. For the very smallest quantities one must press out the insignificant sample volume with a screw type pipette and then either scrape off the part of a drop which has emerged and is suspended under the tip or cut it off with a sharp edge after carbon dioxide freezing of the drop, whereby the dispersion of sample liquid is prevented which otherwise lowers the precision and the reproducibility.

The transport of the sample to the reaction tube must be done with the carrier body in the same way as the reagent.

2. Addition of reagent to the cuvettes over and above what may exist in the basic solution Reagents of considerable volume, i.e. more than 50 $\mu$l, and in liquid form, are added with a conventional syringe pipette of the type which has a reversing valve which, on a plunger movement, discharges a specific volume of liquid in one direction and, on the reverse movement of the plunger fills the reagent into the syringe pipette from a storage vessel.

Since such addition cannot take place simultaneously with the addition of the basic solution, special hoses are required, usually attached to an inner feed unit (tower) in the machine.

For reagent in solid form, which is assumed to consist of a small quantity which is easily and quickly soluble, as also for the reagents which exist in small volumes, less than 30 μl, ready-made carrier bodies are used which contain the desired quantity of reagent measured with the necessary exactness. These reagent units will also follow the carrier body (without loss of substance) until it arrives in the cuvette, which then contains the basic solution.

3. Basic solution is added through plastic tubes on the inside of the analysis cylinder, the tubes being so arranged that they follow the movements of the inner feed tower. The basic solution is then added through an appropriate syringe pump to the cuvette.

It is thus important that between the sample liquid containers (syringe and hose) there is a device, the carrier body, as intermediate link prior to the cuvette. This prevents the contamination which otherwise may arise when the tip of a hose or pipette is dipped in a solution. In the indicated procedure this carrier body receives, on the one hand, the small quantity of sample and serves as storage vessel during the transport to the liquid in the reaction tube (cuvette) and, on the other hand, has the important function of mixer in the solution.

4. Incubation

The chemical reaction must also proceed at a given temperature. The temperature in the cuvettes is kept constant by automatic variation of the length in time of the electrical impulse. Sets of impulses during a few seconds with about 100 impulses per minute and with a duration of 0.5 – 1.0 sec have proved suitable for the carrier bodies tested.

In the sequel a survey will be given of the various variants which can be selected for an analysis programme, as it is necessary to be able to combine different procedures in order to obtain a good result in different kinds of analyses so that the analysis machine can have an extended use.

Examples will also be given of different analyses which can advantageously be performed with an analysis machine according to the invention.

The technique of combining chemical substances so that a single reagent is sufficient for qualified analysis is being increasingly developed. There are already a considerable number of important chemical analyses which, under suitable conditions, can be performed by this simple means. One then follows a procedure which is largely determined by the quantity of sample material for analysis and the volume of reagent of which the composition has been published by the presenter of the method. As an example of such an analysis may be mentioned the determination:

Example: Determination of total protein in serum by the biuret method modified from that of Weichselbaum: T. E.: An. J. Clin. Pathol. 10 (1946), p. 40
Sample: 8 μl serum
Basic solution: 500 μl with biuret reagent
Photometry at 550 nm 2. Analysis with one reagent and blank (blank determination)

A common complication is that sample or reagent, or both, have a colour or other characteristic which prevents direct measurement of that to which the chemical method relates. Correction for such a disturbance can be made by establishing the disturbance due to colour in a specific quantity of reagent and deducting it from the result of colour measurement for the entire sample or by determining the disturbing colour from the sample separately as a "blank". An analysis machine shall be capable of making both corrections, but also of performing analysis in which both types of disturbance occur simultaneously. An example of such a determination is:

Example: Serum iron determination by direct method, modified from that of Ness M. T. and Dickerson H. C.: Clin. Chim. Acta 12 (1965), p. 579
a. Sample: 100 μl serum
Basic solution: 500 μl nitroso-R-reagent with acetate buffer solution
b. Blank 100 μl serum SURVEY OF TYPICAL OPERATIONS WHICH ARE COMBINED IN DIFFERENT WAYS FOR AN ANALYSIS

| 1. Sample material (serum of blood plasma) | 2. Incubation temperature | 3. Type of reaction tube | 4. Agitation and mixing | 5. Washing and drying |
| --- | --- | --- | --- | --- |
| 1.1 in precision syringe programmed for desired volumes | 2.1 Variation of length of the electric impulse | 3.1 Plastic tube circular | 4.1 Magnetic agitator | 5.1 Evacuation (only) |
| 1.2 in plastic hose cut in exact pieces | 2.2 Cooling with Peltier element | 3.2 Glass tube, circular | 4.2 Mixing body with magnetic material actuated by coil with intermittent current | 5.2 Evacuation and flushing with reagent |
|  |  | 3.3 Tube with flat bottom (optically ground) |  | 5.3 Evacuation, flushing with water, drying in dry hot air. |
| 1.3 in thin-walled soft plastic hose which is cut in frozen state | 2.3 Through temperature-regulated water flowing around the reaction tube | 3.4 Square cuvette |  |  |
|  |  | 3.5 Ditch-shaped bottom (for very small volumes) |  |  |

1. Analysis with only one reagent (basic solution)

The simplest procedure is that a specific quantity of sample to be analysed is mixed with a specific quantity of a single reagent, thereby forming or extinguishing a colour.

Basic solution: acetate buffer solution
Photometry at 720 nm. Automatic correction for reagent colour and serum blank.

3. Analysis with corrosive and volatile reagent

A reagent sometimes contains corrosive or malodorous constituents. For automatic analysis it is seldom possible in such case to work in open tubes, as corrosive vapors might attack the apparatus. The analysis machine has been furnished with devices which allow analysis by "acid methods" with volatile reagents etc.

One of the commonest methods in clinical chemistry, the determination of cholesterol in serum, may serve as example.

Example: Determination of total quantity of cholesterol and serum, modified after Zurkowski P.: Clin. Chem. 10 (1964) 5, p 451–453.
Sample: 1 μl serum
Basic solution 500 μl sulphuric acid acetic acid acetate reagent The reaction tubes are covered with a teflon disc which does not follow the cylinder movement and has holes for additions of sample and reagent, washing and photometry.
Photometry at 575 nm.

4. Analysis after dilution for special analysis

Certain physico-chemical analysis methods may be used directly on the sample material, but usually some simple procedure is required such as dilution to a suitable concentration, possibly combined with addition of reagent chemicals. Electrochemical methods arer becoming increasingly common, but analysis of metals is still the completely predominant method. By way of example is cited:

Example: Flame photometric determination of Na, K, Ca and other metals in serum.
Sample: 8 μl, serum (for certain trace metals a larger quantity)
Basic solution: 500 μl 0.65 M is isopropanol. After measurement of, for example, Ca in the dilution (approx 1:60), further dilution by addition of deionized water for determination of, for example. Na (at dilution 1:200).
Flame photometry with three corrections, namely narrowband interference filters (for example for Ca 622 nm, for K 767 nm and for Na 585 nm), fixed corrections for interference between the spectra of different metals, and individual correction for each serum in respect of the effect on the serum concentration of the various metals.

5. Analysis after dilution of sample and delayed addition of reagent

Often reagent must be added in a specific time sequence. The analysis machine therefore has the means of adding reagent in specific positions, i.e. at specific times. One of the commonest clinical chemical forms of analysis may serve as example, namely Example: Determination of "blood sugar" by analysis of the glucose content in serum according to Heedman's (unpublished) modification of Raabo, E. and Terkildsen, T. C.: Scand. J. Clin. Lab. Invest. 12 (1950), p 62
Sample: 5 μl serum
Basic sol: 300 μl distilled water
Reagent: (which is added in a position 8 min prior to photometry): 150 μl glucose oxidase-orthotoluidine-peroxidase reagent.

6. Analysis with basic solution and reagent in mixer.

Sometimes it may be advantageous to add reagent in solid form. This requires that the analysis machine performs effective mixing and that the reagent quickly dissolves. As example of such a method is cited:

Example: Creatinine determination in serum, essentially in accordance with Henry's textbook (Henry, R. J.: Clinical Chemistry (1964), p. 292.
Sample: 40 μl serum
Basic solution: 500 μl 0.15 M NaOH
Reagent in the mixer body: 2.3 mg picric acid.

In the analysis serum and NaOH are first mixed, followed immediately afterwards by the main part of the picric acid. The time for the photometric reading (at 15560 nm) can be so assigned that a kinetic determination is made, if so desired, instead of conventional reading at a later stage.

7. Analysis with several reagents in sequence

Some analyses may, in respect of the reagent, be specially exacting and require high precision and exact time intervals. As example of analyses with such sequences of addition of reagent is cited the following:

7.1 Example with solid and liquid reagents: Determination of "iron binding" capacity (TIBC) by the TPTZ method according to Schade A. L., et al., Proc. Soc. exp. Biol. Med 87 (1954), p. 443.
a. Sample: 80 μl serum
Basic solution: 380 μl tris buffer, pH 8.5
Reagent: in a mixer body: 0.4 μg Fe in 5 μg 0.01 M HCl
Reagent with TPTZ: 120 μl
b. Blank: 80 μl serum
Basic solution: 385 μl tris buffer, pH 8.5
Reagent with TPTZ: 120

7.2 Example with three reagents: Determination of urea in serum with Berthelot's reaction modified according to Kaplan, A: Stand. Methods Clin. Chem 5 (1965), p. 245–256.
Sample: 1.5 μl serum
Basic solution: 50 μl distilled water
Reagent:
 1. in mixer body: 0.02 unit urea (sigma) in 2 μl EDTA buffer
 2. with phenol: 225 μl
 3. with hypochloride: 225 μl
N.B. Phenol and hypochloride reagents are added from an inner tower.
Photometry at 560 nm.

8. Enzyme determination with one- or two-point analysis (so-called colorimetric determination).

Medical laboratory diagnosis is becoming increasingly directed to determinations of enzyme activities. The simplest methods, and the commonest in routine work, are based on determination of the difference of concentration before and after a time of enzyme action. Even if in certain cases an analysis machine should be able to permit the use of a more advanced method of determination, an analysis machine must be usable for routine analyses. With small alterations the technique can be varied for different purposes. Here is cited as example of an ordinary clinical analysis.

Example: Determination of GPT (glutamic acidpyrodruvic acid-transaminase, aminoferase) modified from Reitman S., Frankel S., Am. J. Clin. Pathol. 28

(1957), p. 56.

By change of substrate GOT can be determined and with small changes for a large number of enzymes and substances.

Sample: 5 μl serum
Basic solution: 40 μl substrate in phosphate buffer, pH 7.40
Reagent 1: 40 μl dinitrophenyl hydrazine in hydrochloric acid
Reagent 2: 420 μl 0.4 M NaOH
Photometry at 505 nm 9. So-called kinetic determinations (see description with reference to FIG. 9).

Measurements of processes of enzyme reactions are in great demand. For rapid analysis machines this implies difficulties, since the enzyme activity in blood serum in different morbid conditions may vary very greatly and it is difficult to combine demands for rapidity of analysis with the desire to observe an enzyme process during a given time, at least for a minute or so. As a rule it has proved most favourable, therefore, to have special analysis machines for the so-called kinetic determinations.

The suggested analysis machine combines two procedures by following the initial enzyme action during a short time and, if the enzyme activity is high, by determining it. One can also measure the enzyme action on the same sample after a lengthy time and thus fully automatically obtain values also for low enzyme activites. There is a great demand for so-called kinetic determination of enzyme and the analysis machine can be furnished with accessories which permit these measurements. Many enzyme determinations are commonly made in clinical laboratories and here lactic acid dehydrogenase is cited as example.

Enzyme determination from repeated measurements in long-wave ultra-violet light (340 nm) modified according to Wroblewski F. et al., Proc. Soc. exp Biol. Med. 90 (1955), p. 210.

The method requires a 6-cell photometer, a sextuple valve in order to be able to dispense five successive samples to different cuvettes. Each sample can then be kept during five work cycles in its cuvette for consecutive measurements during that time. Much later, furthermore, immediately before washing, part of the remaining reaction quantity is transferred also to the sixth photometer cuvette for final measurement.

Example: LDH (Lactic Acid Dehydrogenase), but by change of the substrate the method can be used for a large number of enzymes, nicotinamide-adenine-dinucleotide being oxidized or reduced so that a change in light absorption takes place which can be measured and followed. The conditions are given for room temperature.
Sample: 10 μl serum
Basic solution: 500 μl, substrate
Reagent: 25 μl pyruvate reagent which initiates the reaction.

A microcomputer calculates the mean value of the change of absorbance per minute, checks that the process has been linear and decides whether the last value is needed for sufficient exactness (at low enzyme activity).

The analysis machine itself will now be described.

FIG. 3 shows in perspective the central analysis unit of the machine, namely cylinder 1 in perspective. The external feed unit or tower 2 conceals a part of the cylinder, while an internal feed unit or an internal tower 6 appears above the upper edge of the cylinder. The cylinder 1 may be made of metal, for example aluminium or copper, or of plastic and on its outer surface has a number of metal rings in meander or toothed pattern. The various tooth-shaped projections 7 are intended as seatings for the test tubes or cuvettes and for this purpose are furnished with vertically drilled holes 8. The rings form a number of planes lying one above the other — each plane being intended for use for one type of analysis — the teeth on the various planes being displaced one step in relation to one another so that on each overlying plane a gap is formed through which access is obtainable to a cuvette on the plane below. In this way the entire cylinder obtains to some extent the appearance of a cylindrical honeycomb.

On its lower edge the cylinder has a driving gear-ring 9 which is intended for stepwise feed of the cylinder in the direction of the arrow P. In the example shown the cylinder is imagined to have 50 steps with a stepping rate of two steps per minute. One would thus have available a reaction time of 25 minutes for reaction components inserted in the cuvettes.

Thus, whereas the various cuvette planes are reserved for the various kinds of analyses, the various cuvettes in a column of cuvette seatings are intended for a single object, for example a patient sample. If the cylinder, accordingly, is thought to have 20 planes, one can simultaneously dispense a patient sample to 20 planes and thus subject the sample to 20 kinds of analysis. In the arrangement of the cuvette seatings shown in FIG. 3 the height of the cylinder would then be 40 planes, since only each second plane in a column can be used by a cuvette.

To permit direct photometry on the reagent mixture, the various cuvette seatings have radial through-holes 10. There are also arranged in the cylinder additional radial holes 11 through which pipetting can be done with pipettes 12 arranged on the internal feed tower 6. On the internal tower there are also lamps 29 for direct photometry through holes 10. The various cuvette rings may suitably be divided into a number of segments, e.g. four, and e.g. by means of screws fixed in the cylinder.

It is obvious that cylinder 1 must be controllable by some bearing on the table 4 in FIG. 1, although no such bearing has been shown in the drawings. Likewise it is necessary to have some form of holders which slide on the upper edge of cylinder 1 and keep it upright. One may imagine two or three such holders arranged on posts which are easily swung out so that the cylinder with cuvettes can be readily lifted up for inspection, and to permit inspection also of the feed units or feed towers 2 and 6. The latter may also be duplicated and confronted or placed in inverted relation to one another, so providing an arrangement which in cross-section is shown in FIG. 5 and viewed from above in FIG. 6. In this case it is advisable to double the cylinder periphery so as to complete one reaction process during a movement of the cylinder corresponding to half the periphery.

The function of the internal feed unit or tower 6 is to dispense basic solution, which in FIG. 3 is imagined to take place by means of the two pipettes 12 on the left.

The functions of the external tower are the dispensation of sample substance and reagent, which is imagined to take place by means of elevators 14 which interwork with sets of vertical feed arms 15, the raising of carrier bodies from the cuvettes with preferably magnetic arms 16 after completion of the reaction process, direct photometry by means of lamps 29 on the internal tower and sets of photocells 17 arranged in stacks on the external tower, and finally washing and rinsing of the cuvettes in their final position by means of the rinsing nozzles 12' on the righthand columns in the internal tower 6 and corresponding columns of evacuation devices 18 on the external feed towers 2.

It also has on the internal feed tower electrical leads for delivery of impulses for feed to coils 34 in the cuvette seatings (FIGS. 7 and 8) intended to actuate the carrier bodies in the cuvettes for agitation of the reagent mixture.

As already noted, it is characteristic of the analysis machine according to the invention that a large number of devices — cuvettes — have been combined on a common surface so that all together can be moved by means of a simple movement mechanism, as also that a large number of feed devices and service devices are combined on the external feed tower 2 and on the internal feed tower 6. For simultaneous movement of all devices on the feed towers in towards the cylinder surface with the cuvettes and out from it the towers are movable in their entirety. This provides an extremely massive and concentrated effect in every phase of movement of the analysis machine.

FIG. 5 indicates how the movement of towers 2, 6, 6' and 2' can be controlled by means of a common endless screw 19 which can be operated by means of a reciprocating motor 20. In this simple way, accordingly, as a result of the direction of thread in the engagements with the drive nuts in the various towers, one obtains a movement of the towers 2 and 6 and of 2' and 6' in towards the cylinder wall and out from it. By allowing the towers to move up and down in relation to their drive nuts on the endless screw 19 and by simultaneously steering the movement of the towers with a cam 23 and ball-shaped rollers 24 on the towers one can also obtain a reciprocal motion of the towers, as indicated in FIG. 3 by arrows P1 and P2. In this way, as will be readily realized, pipettes and nozzles 12 are introduced into the cuvettes, as well as reagent units and sample substance doses, by means of the sets of arms 15.

In FIG. 3, for the sake of simplicity, the various feed, service and pipette devices are shown to have radial directions; in reality, however, they must be arranged in parallel in order to permit the simultaneous parallel movement of all devices.

Furthermore, in reality towers 2 and 6 must be one level higher than cylinder 1 in order to be able to feed and serve also the uppermost level, but for the sake of simplicity the towers are shown in FIG. 3 as being on the same level as the cylinder.

In FIG. 3 the feed of reagent units and test substance doses is indicated entirely schematically through two feedways B1 and B2 which bring up a number of carrier bodies 25 which are considered to consist of reagent units, on which accurately measured doses of sample substance have also been added in the laboratory. It is assumed that the carrier bodies contain magnetic material and therefore that, when the bodies are brought into their paths, one can successively grip the carrier bodies with arms 26 on the elevator 14 which, every time it has gripped a couple of carrier bodies, is raised up a double step so that two new arms 26 can grip two new carrier bodies. In this way, accordingly, all arms 26 on elevator 14 will be furnished with carrier bodies when the elevator reaches its topmost position. It is thereafter turned in the direction of the arrow P3 and delivers all carrier bodies to the set of feed arms 15. It is assumed that there are two elevators 14, so that both sets of arms 15 can be furnished with carrier bodies.

Simultaneously with the feed of two columns in this way by means of the feed sets 15, washing of two preceding columns is done with the two washing sets 12', 18 on the right in the internal and the external tower, at the same time as basic solution has been dispensed to the first two columns through the two sets of pipettes 12 on the left in the internal tower. At the same time photometry is done in the two preceding columns.

One may thus say that these initial measures for starting a set of analyses for a given sample take place simultaneously with the measurements for a set of analyses relating to another sample and simultaneously with the final measures on the cuvettes used for a set of analyses in respect of a third sample.

Another advantage of the invention is that there are essentially only three movable, alternatively five movable, parts in the analysis machine which need to be controlled, namely the cylinder and an external and an internal tower, alternatively two external and two internal towers. One therefore obtains very simple supervisory means and simple control electronics.

The cuvettes need not be moved out of their seatings but sample and reagent are fed into the same cuvettes, which thereafter serve as reaction vessels and also as measuring vessels. By means of a microcomputer one can then introduce the corrections necessitated by differences in the optical characteristics of the cuvettes. Regulation of the temperature conditions during the reaction and the agitation or mixing is also done in the same cuvettes, since the cuvette seatings are furnished with coils which are fed with pulsating or alternating current which actuates magnetic material in the carriers lowered into the cuvettes. Thus agitation is obtained both by regulation of the length of the impulses and also by regulation of the reaction temperature.

FIGS. 5 and 6 indicate in rather greater detail how the driving of the cylinder 1 by means of gearwheel 27 via the gear-ring 9 can take place, and how the various towers 2, 6, 6' and 2' are driven and how they can be made available for inspection.

The various towers are steered in vertical U-shaped guides 53–56. In such case, when the shaft 19 with the endless screws is driven by the motor 20, the towers will accordingly be lowered, as the balls 24 successively slide down from the plane surfaces of the cam surface, through the fact that the screws engage with the nuts 22 in the lower portions of the U-shaped guide. In the same way the towers will be raised when the shaft 19 is driven in the opposite direction.

Over a part of their length, corresponding to the height of the towers, the guides can be swung out sideways around the piano hinges 53" – 56" so that the towers 2, 6, 6' and 2' as well can be swung out in the positions shown by dashes in FIG. 6. The feed, measurement and control devices of the towers thus become available for inspection.

FIGS. 7 and 8 indicate how the direct photometry can take place.

According to FIG. 7 the cuvette 28 is illuminated by the rays from a lamp 29 through the lens 33 and hole 10, and after passing the reagent mixture 30 the beam of light enters a photometer 17 which transfers the result electrically to a microcomputer for evaluation and transfer to the printer.

According to the alternative shown in FIG. 8 a glass body 31 is instead immersed in the reaction mixture 30; the body 31 has a ground surface 32 against which the beam of light is directed from the light source 29 via a lens 33 and the hole 10 in the cylinder wall 1. If in the latter case the glass body or glass rod is made movable within certain limits in a guide in a bracket 39, one can imagine making measurements of the turbidity and colour of a bottom sediment, which is of great interest, for examples, for serological measurement with precipitin reactions. If, in the proposed manner, the rod is slowly moved towards the bottom, there is initially no change in the reading, but as one approaches the bottom of the vessel the reading increases asymtotically and thus produces a reliable measurement. One can combine this measurement procedure with a comparator and then obtain an extremely suitable method for blood group determination through the so-called haemaglutinin reaction. In FIGS. 7 and 8 coils 34 have also been drawn with which agitation in the reaction mixture and regulation of its temperature can take place in the manner earlier referred to.

FIG. 4 shows another embodiment of the invention. In this case the cylinder 1 is furnished with cuvette holder rings 7 which have cuvette seatings 8 for every step of the movement of the cylinder. The cuvette holder rings 7 are arranged at a given distance from one another in order that the cuvettes may be accessible for pipettes and nozzles for feed of reagent units and sample substance doses. External tower 2 and internal tower 6 are only schematically indicated. As in the earlier described embodiment, in this case as well the cylinder has through-holes 10 for optical measurement and holes 11 to provide access from the inside of the cylinder to the cuvettes for pipettes 12 and nozzles 12'. The function of the devices 29 and 17 for direct photometry is the same as earlier indicated in conjunction with the description of the embodiment according to FIG. 3. Likewise washing and rinsing of the cuvettes after completion of the analysis take place through the right-hand nozzles 12' on the internal tower 6 and the devices 18 in the same way as earlier described. As regards the dispensation of sample substance and reagent, however, this is assumed to take place somewhat differently in this case than earlier described.

The sample substance to be analysed, for example serum, is inspected in respect of quality and sufficiency of the samples and is suctioned up into a dispensing syringe as described earlier. The syringes 58 are freed from air and placed in holders so arranged that in one position the syringe can deliver through a bent tip a small quantity of serum as sample volume.

The measured quantity of serum, the volume of which may vary depending on the analysis, is placed in a carrier of essentially the same type as the earlier described carrier body with or without reagent. The carriers are kept in cassettes 35 so shaped that the carriers 25 can be removed one by one to a feed device which transports the carriers 25 up to a double sample elevator 14. Each elevator may, for example, be so shaped that it consists of a half cylinder which in its domed portion has recesses with grooves and shoulders to take up and accommodate the carriers. Each half cylinder has a number of such recesses corresponding to the number of planes in the cylinder, so that on upward movement it successively fills a carrier for each plane, i.e. for each type of analysis. The half cylinders are so arranged that they have an alternating function, i.e. one moves upwards and successively fills carriers, as already described, while the other half cylinder supplies carriers to the feed arms 15, which transfer them to the cuvettes, and then returns to starting position. The function is made possible through the fact that the half cylinders rotate half a turn so that they can alternatively be charged with carriers 25 on the way up or deliver them to the feed arms, which transfer them to the cuvettes on the respective planes.

The holder for the dispensing syringes 58 can be arranged for throw-away syringes, the holder being automatically emptied of syringes after the dispensation and serving as store for the remaining quantity of sample solution. For other syringes automatic cleaning is arranged through repeated rinsing.

As regards the reagent units, these are fed in through cassettes 35, which are introduced at the various levels, so that the various reagent carriers are in due course fed into the feed devices 15 on the various levels and are magnetically dispensed into the cuvettes.

As is seen, the cassettes 35 are so shaped, that packages arranged in parallel, for example by spring pressure, can press forward one reagent carrier at a time so that it is easily withdrawable through the feed device 15.

During storage the cassette 35 is closed and by suitable means can be given the atmosphere favourable to the reagent. For use a small cover is removed at the opening of cassette 35 and, by means of slide-grooves and snapp-fasteners, it can be connected to the point of use on the level in question. Both the carrier body 25 and the cassette 35 may suitably be made of plastic and contain no other magnetizable material than exists in the carrier bodies.

In cases when it is desired to make special measurements, this is also possible according to the invention. FIG. 9 shows an example of so-called kinetic photometry which is suited for determinations according to the earlier described example 9.

One sees in this case that, from the cuvettes 28, a given quantity of reaction mixture is fed successively, as cylinder 1 steps forwards, from the various cuvettes 28 through a multiple valve 37 and a suction pump 38 connected to it. In this way the reaction mixture is distributed among six photometers and can thereafter, through use of the latter, determine the change of enzyme acitivity.

Since in every working cycle there is a new sample in cuvette 28, which is filled into the photometer vessels by the suction device, a second sample will be suctioned into the second photometer, the third sample into the third photometer, the fourth sample into the fourth photometer, the fifth sample into the fifth photometer and the sixth sample into the sixth photometer. Subsequent samples will successively replace earlier ones, starting again in the first, second etc. photometer. Each sample must therefore remain in a photometer during six working cycles, which allows following of the reaction during its first stage.

Most important is that a certain quantity of the reaction mixture is left in cuvette 28 on each occasion.

FIG. 10 shows a diagram illustrating what is to be determined, i.e. the absorbance A as function of time T. One measures the consumption of NADH in the reaction at 340 nm, which is one of the most common procedures, see example 9 above.

In the case of high activity one can obtain, by means of successive measurements, a measure of the slope of the curve corresponding to the enzyme acitivity. The slope may be so steep that the substrate is consumed after only a minute or so. In this case the effect is great and easy to measure.

The difficulty is, instead, if the enzyme activity is low, which is common in normal cases. In such case the effect during the first minutes will be too small for estimation and one must make a determination also after a considerably longer time.

The remaining quantity in the cuvettes 28, therefore, is subjected to the same reaction. Since, at the end of a revolution of the cylinder (with suitable arrangement and duplication of analysis channels possibly two revolutions), and the introduction of the reaction mixture in a further cuvette, the latter point in the reaction process can be established.

In purely general terms it should be recognized also that the method of using predivided reagent doses often places great demands on exactness, and in such case it is to be noted, that this applies to the final quantity of reagent. Durability is also a factor and, to increase it, one can count on being able to preserve individual doses, often dry, of reagent chemicals better than in solution.

The quantities usually involved in analyses in which the reaction volume in the final measurement is around 0.5 ml (500 μl) amount to about 0.5 – 50 mg. This means that the absolute error may at times be at most 1 μg, e.g. 0.20 mg ± 0.001 mg (200 ± 1 μg).

In principle the use of reagent units implies that the exactness must be attained in the manufacture instead of in the analysis.

In the sequel examples will be given of chemicals etc. which are required for analyses and which may be used in reagent units, and of the procedure and of the various alternatives between which the laboratory may choose.

The chemicals may have amorphous or microcrystalline form in order to easily solute. Inert substances having a very high solubility may be added.

A. Chemical substances

DL-Alanine
4-Aminoantipyrine = 4-amino-1.5-dimethyl-2-phenyl-3-pyrazolone
2-Amino-2-methyl-1-propanol
Ammonium hepta-molybdate, 4 aq.
Ascorbic acid
Bromcresol green = 3.5′, 5.5′-tetrabromo-m-cresol sulphon phthalein
Brij 35 = polyethylene lauryl alcohol
Citric acid, 1 aq.
Caffeine
O-Dianisidine = 3.3′-dimethoxybenzidine
Dextran sulphate
EDTA = ethylene diamine tetra-acetic sodium salt
Fast Red B salt = 5 nitro-2-amino-methoxybenzene diazotate, Sigma
Phenol
Phenyl phosphate di-sodium salt
Hydroquinone
HBAB = 2-(4′-hydroxybenzazo)-benzoic acid
INT = 2-(4-iodophenyl)-3-(4-nitrophenyl)-5-phenyl-tetrazolium chloride
Isopropanol = 2-propanol
Dipotassium hydrogen phosphate
Dipotassium oxalate, 1 aq.
Potassium-ferricyanide = potassium hexacyanoferrate (III)
Potassium-sodium-tartrate, 4 aq.
alpha-ketoglutamic acid = 2-oxo-glutamic acid
Copper sulphate, 5 aq.
Magnesium chloride, 6 aq.
Magnesium sulphate, 7 aq.
DL-Lactic acid, 85 % by weight (DL-Lactic acid 85 % W/W)
L-Lactic acid, 98–100 % by weight (L-Lactic acid 98 %–100% W/W)
NAD = Nicotinamide adenine dinucleotide
NADH = Reduced nicotinamide adenine dinucleotide
alpha-Naphthyl phosphate = sodium naphthyl(1) phosphate
Sodium acetate
Sodium azide
Sodium benzoate
tri-Sodium citrate, 2 aq.
Sodium hydroxide
Sodium hypochlorite
Sodium carbonate
Sodium nitrite
Sodium disulphite (Na2-S2-O5)
Sodium sulphite
di-Sodium tetraborate, 10 aq.
Neocuproine = 2.9-dimethyl-1, 10 phenanthroline
di-Nitrophenylhydrazine = 2.4-dinitrophenylhydrazine
Nitroprussid sodium, 2 aq. = disodium pentacyanonitrosyl ferrate
Nitroso-R = 1-nitroso-2-hydroxy-3.6-naphthaline-disodium-sulphonate
PMS = 5-methyl-phenazinium methyl sulphate
Picric acid
Sulphanilic acid
5-Sulphosalicylic acid, 2 aq.
TPTZ = 2.4.6-tri(2-pyridyl)-1.3.5-triazine
TIBC
Thymol
Zinc sulphate, 7 aq.

B. Standards

1. For the preparation of primary absolute standard solutions the following examples may be given:
They require an extreme exactitude of the unity doses.

Pyruvic acid
Glucose
Ferrinitrate, 9 aq.
Calcium carbonate
Potassium dihydrogen phosphate
Potassium nitrate
Cholesterol
Creatinine
Lactic acid
NADH (reduced nicotinamide adenine dinucleotide)
Sodium nitrite
Oxaloacetic acid
Uric acid
Urea 2. Certain primary standards require control analyses. This is true with respect to the following examples:
Albumin, human and animal serum albumin
Bilirubin
Enzyme preparations, such as amylase, various esterases, glycose oxidase, peroxidases, urease, uricase
Hemoglobin derivatives such as oxihemoglobin, cyanhemoglobin
Combinations for multiple channel analyzers.
Apparatus standards and chemical mixtures for control of the apparatus function, for instance photometry (Colorimetric standard)
Standard serum preparations, commercially available with different concentrations and enzyme activities.

C. Reagents in buffer solutions.

A chemical reaction very much depends on the acidity and also on the ion density. The acidity, pH, is given by the relation between acidity and basicity, while the absolute amount or concentration is of minor importance within certain limits.

These reagents are often used in the basic solution. The following examples give an idea of what is used.

Citric acid/sodium hydroxide, barbital/barbital sodium, EDTA/sodium hydroxide, glycin/sodium hydroxide, primary and secondary orthophosphate of sodium or potassium salts, tris buffer base/tris buffer hydrochloride and acetic and sodium acetate.

Examples of procedure for use of reagent unit in chemical analysis.

EXAMPLE 10

Evaluation of alternative means for determination of the creatinine content in blood serum with Jaffe's picrate reaction. The alternatives differ as regards the composition of the basic solution.

1. Basic solution, 500 $\mu$l containing alkaline picrate to which is added 40 $\mu$l blood serum.
2. This alternative is the commonest for analyses in large series and thus especially for automation. Its main disadvantage is the poor durability of the reagent, which undergoes continuous disintegration. The need for precision determines whether the reagent must be prepared daily or several times a day. Preferably the reagent should always be newly prepared.
3. Basic solution in form of 500 $\mu$l 0.15 M NaOH to which, after mixture, is added a reagent dose of 2.3 ± 0.01 picric acid which, through effective mixing, is quickly dissolved and then reacts with the creatinine.
4. Basic solution in form of 500 $\mu$l pure water, to which, as reagent unit, is added 40 $\mu$l blood serum and 3 ± 0.015 mg NaOH. Through effective mixing the sodium hydroxide is dissolved and mixed with the serum sample. Thereafter 2.3 ± 0.01 mg picric acid is added to the reagent unit.

In all alternatives photometry is done at 560 nm wavelength and one has the choice of so-called kinetic determination, i.e. the use of the first part of the reaction time as best expression for the creatinine concentration or, by the old conventional method, reading of the formation of reddish colour after a specific, somewhat longer time, in which case, however, certain nonspecific side-reactions with elements which are not creatinine are more or less included.

Evaluation
Under given conditions alternatives 2 and 3 are best from the analytical point of view but require reagent units and effective mixing. The choice between 2 and 3 would probably depend on whether basic solution containing 0.15 M NaOH is used (for other analyses performed simultaneously). Practical and economical reasons would appear to favour this procedure. Pure water is a common additive.

EXAMPLE 11

Determination of the enzyme activity for so-called alkaline phosphatase in blood serum.

Of various methods available for determination of this enzyme activity the choice has been to determine the quantity of phenol which is enzymatically liberated from phenyl phosphate under standardized conditions and during a given time, after which the reaction is interrupted and a red quinone is formed by chemical reaction with 4-aminoantiphyrine (AAP) and potassium ferricyanide.

The following alternatives may be considered:

1. Conventionally the method is that, to 400 $\mu$l of a basic solution containing a borate/carbonate buffer with magnesium addition for optimal enzyme effect and containing 0.44 ± 0.002 mg sodium phenyl phosphate as substrate, is added a quantity of 6 $\mu$l blood serum. After mixing, the enzyme is allowed to act during a specific time, after which 0.61 ± 0.006 mg AAP is added, for example in 50 $\mu$l water, and 4.8 mg potassium ferricyanide, for example in 50 $\mu$l water.
2. To a basic solution of borate/carbonate buffer with magnesium activator is added a reagent unit containing 6 $\mu$l blood serum and a quantity of 0.4 ± 0.002 mg sodium phenyl phosphate. After incubation a reagent unit is added containing 0.61 ± 0.006 mg AAP and a reagent unit containing 4.8 mg potassium ferricyanide, possibly in the same reagent unit.

In both cases the determination is made by photometry at 505 nm and the activity is indicated in units based on the quantity of phenol liberated in the reaction.
Evaluation
The latter alternative is superior, as the critical reagent consists of sodium phenyl phosphate in solution and has poor durability. On the other hand the buffer solution is durable and it is advantageous to have the enzyme substrate separate and in dry form, in addition to the gain of not needing to take into account that in the analysis the pipetting will not be completely successful and exact.

Although the invention has been described with reference to a number of its embodiment, it can nevertheless be arbitrarily varied within the scope of the following claims.

What is claimed is:

1. A method for the simultaneous performance of a number of analyses, comprising disposing a multiplicity of receptacles for analysis of treated samples in a fixed relationship in vertical columns and horizontal planes to form a receptacle array in mating interfacial juxtaposition to similarly disposed arrays of operative means comprising reagent dispensing means, sample dispensing means, treatment means, analytic means, and receptacle cleaning means respectively such that individual operative means are coordinately positioned for simultaneous engagement with a multiplicity of receptacles; said receptacle array is periodically progressed laterally in stepwise manner to maintain said juxtaposed relationship in a series of spaced positions; executing steps in the analytic sequence simultaneously with said operative means, respectively upon a multiplicity of selected individual receptacles, in sequence at each of the progressive positions whereby individual receptacles are simultaneously progressed in a series of steps through a cycle of sample treatment and analysis to cleaning.

2. The method of claim 1, wherein a wet chemical analysis is employed utilizing photometric analytic techniques upon individually calibrated cuvettes.

3. The method of claim 1, wherein the horizontal planes of receptacles are associated with a specific analytic object, and the vertical columns of receptacles are associated with a specific subject.

4. The method of claim 1, wherein reagent is supplied in the form of reagent unit dosages constituted by a precise quantity of reagent in association with a carrier therefor comprising magnetic material.

5. The method of claim 4, wherein the individual receptacles are agitated by the action of a magnetic field upon the reagent unit dosages.

6. The method of claim 4, wherein at the completion of the desired reaction, the carrier is removed from the receptacle by magnetic means.

7. An apparatus for the simultaneous performance of a series of analyses upon a multiplicity of samples comprising a support providing an array constituted by a multiplicity of cuvette receptacles in fixed vertical columns and horizontal planes to form a checkerboard configuration;

at least one dispensing means providing a plurality of dispensing stations in a series of fixed vertical planes, said stations being individually displaceable, respectively, along the said vertical planes;

said support and said dispensing means being in upright facial juxtaposition; and being relatively displaceable horizontally to simultaneously engage respective dispensing means in a series of vertical planes with a multiplicity of cuvette receptacles supported in a series of juxtaposed vertical columns;

at least one analysis means providing a plurality of analysis stations capable of simultaneous engagement with the said cuvette receptacles at a plurality of the said fixed positions thereof, whereby upon relative horizontal or vertical displacement of sample receptacles dispensers and analysis means, a multiplicity of analytic sequences can be performed simultaneously.

8. The apparatus of claim 7, further comprising means for controlling temperature and degree of agitation within the supported cuvettes, means for analysis of individual supported cuvettes, and means for cleaning individual supported cuvettes.

9. The apparatus of claim 7, further comprising a multiplicity of electric coils associated with the individual cuvette receptacles.

10. The apparatus of claim 7 wherein the cuvette receptacles are formed in and about an arcuately curved surface to form a cylinder.

11. The apparatus of claim 10, wherein the cylinder is mounted through an axial bearing engaging the periphery of said cylinder for rotational movement thereof, and is driven through a gearing mechanism in a stepwise manner.

12. The apparatus of claim 10, wherein the cylinder is hollow, and at least one additional upright juxtaposed feed unit for the cuvette receptacles is located within said cylinder.

13. The apparatus of claim 12, wherein the dispensing means and feed units, respectively, are movable toward and away from engagement with the cuvette support.

14. The apparatus of claim 12, wherein the dispensing means and the feed unit are arcuately curved in a matching manner to the cuvette support such that several columns of cuvette receptacles are in juxtaposition with individual dispensing and/or feed means simultaneously.

* * * * *